United States Patent
Chan et al.

(10) Patent No.: US 10,527,406 B2
(45) Date of Patent: Jan. 7, 2020

(54) DEVICE AND METHOD FOR DETERMINING THE LOSS ON IGNITION OF AT LEAST PART OF AN IRON AND STEEL PRODUCT

(71) Applicant: FIVES STEIN, Maisons Alfort (FR)

(72) Inventors: Yuen Yee Chan, Evry (FR); Jean-Luc Magalhaes, Boissy sans Avoir (FR)

(73) Assignee: FIVES STEIN, Maisons Alfort (FR)

( * ) Notice: Subject to any disclaimer, the term of this patent is extended or adjusted under 35 U.S.C. 154(b) by 205 days.

(21) Appl. No.: 15/548,592

(22) PCT Filed: Feb. 4, 2016

(86) PCT No.: PCT/IB2016/050567
§ 371 (c)(1),
(2) Date: Aug. 3, 2017

(87) PCT Pub. No.: WO2016/125096
PCT Pub. Date: Aug. 11, 2016

(65) Prior Publication Data
US 2018/0017374 A1    Jan. 18, 2018

(30) Foreign Application Priority Data
Feb. 4, 2015    (FR) ..................... 15 50878

(51) Int. Cl.
*F27D 19/00* (2006.01)
*G01B 11/06* (2006.01)
(Continued)

(52) U.S. Cl.
CPC ............. *G01B 11/06* (2013.01); *C21D 1/74* (2013.01); *C21D 1/76* (2013.01); *C21D 11/00* (2013.01);
(Continued)

(58) Field of Classification Search
CPC ................................ B21B 45/08; G01B 11/06
See application file for complete search history.

(56) References Cited

U.S. PATENT DOCUMENTS

| | | |
|---|---|---|
| 3,250,119 A | 5/1966 | Roberts |
| 2016/0107214 A1* | 4/2016 | Clark ................. B21B 45/08 72/12.7 |
| 2018/0017374 A1* | 1/2018 | Chan ................. C21D 11/00 |

FOREIGN PATENT DOCUMENTS

| | | |
|---|---|---|
| EP | 0 767 353 A1 | 4/1997 |
| KR | 2012 0032870 A | 4/2012 |

(Continued)

OTHER PUBLICATIONS

International Search Report, dated Apr. 11, 2016, from corresponding PCT/IB2016/050567 application.

(Continued)

*Primary Examiner* — Scott R Kastler
(74) *Attorney, Agent, or Firm* — Young & Thompson

(57) ABSTRACT

Disclosed is a method and device for determining the loss on ignition of at least part of an iron and steel product during passage through a furnace upstream of a descaler. The device includes electromagnetic sensors, with at least one arranged to scan the product's lower surface near the furnace outlet, the sensor oriented so the scanning plane of the electromagnetic radiation from the sensor is perpendicular to a direction of movement; a set of at least two electromagnetic sensors upstream of the descaler, oriented so their scanning planes are substantially on a single plane perpendicular to the direction of movement of the at least part of the product; and at least two electromagnetic sensors downstream of the descaler, oriented so their scanning planes are substantially on a single plane perpendicular to the product's (Continued)

movement direction. The sensors determine the height of the product upstream and downstream of the descaler.

14 Claims, 4 Drawing Sheets

(51) Int. Cl.
| | |
|---|---|
| *C21D 11/00* | (2006.01) |
| *F27B 9/40* | (2006.01) |
| *C21D 1/74* | (2006.01) |
| *C21D 1/76* | (2006.01) |
| *G01N 21/95* | (2006.01) |
| *G01N 33/20* | (2019.01) |
| *G01G 19/03* | (2006.01) |
| *G01G 17/00* | (2006.01) |

(52) U.S. Cl.
CPC ............... *F27B 9/40* (2013.01); *F27D 19/00* (2013.01); *G01N 21/95* (2013.01); *G01N 33/20* (2013.01); *F27D 2019/0003* (2013.01); *F27D 2019/0034* (2013.01); *F27D 2019/0068* (2013.01); *G01G 17/00* (2013.01); *G01G 19/035* (2013.01); *G01N 2201/06113* (2013.01)

(56) References Cited

FOREIGN PATENT DOCUMENTS

| KR | 20120096997 A | 9/2012 |
|---|---|---|
| KR | 20130134328 A | 12/2013 |
| WO | 02/088680 A1 | 11/2002 |

OTHER PUBLICATIONS

FR Search Report, dated Dec. 4, 2015, from corresponding FR1550878 application.

* cited by examiner

DEVICE AND METHOD FOR DETERMINING THE LOSS ON IGNITION OF AT LEAST PART OF AN IRON AND STEEL PRODUCT

FIELD OF APPLICATION

The invention relates to a process and device for controlling a furnace for reheating the semi-finished steel products. The device and the process according to the invention make it possible to determine in real time the total oxide scale formed on the semi-finished steel products linked to the reheating of a product in the furnace, by determining the amount of oxide scale that has fallen into the furnace during the heat process and the amount that has fallen after the descaling machine (or descaler). They also make it possible to determine the amount of oxide scale that has remained attached on the product after descaling.

This quantification is carried out by means of electromagnetic sensors, the resolution of which makes it possible to accurately measure the thickness of the oxide scale and determine in real time the scale loss.

PRIOR ART

The invention belongs to the field of furnaces for reheating the semi-finished steel products.

During the reheating of a semi-finished steel product such as billet, bloom or slabs in a heat treatment furnace with a direct flame, the oxidation occurs at the surface of products. The amount, the types and qualities of oxide scale depend on the composition of the steels, on the chemical composition of the combustion gases, on the discharging temperatures, on the residence times of the product in the various zones of the furnace, on the various temperatures in the furnace and on the heating curve of the product along its passage through the furnace. Depending on the values of these various parameters, the oxide scale that is formed at the surface of the product is more or less significant in terms of quality, quantity and characteristic.

The oxide scale, for example between 0.5% and 1% of the weight of the furnace-charged product, leads to a loss of material (scale loss) that is eliminated before entering the rolling mill and that is not therefore converted to finished product (wire, section or sheet), which constitutes an economic loss for the operator of the plant.

Heating of the part of the steel lost in the form of oxide scale leads to a loss of energy, a reduction in the overall efficiency of the plant and an increase in the production cost of the finished product.

The oxide scale may detach from the surface of the products in the furnace during the passage of the products while they are being heated. The accumulation of oxide scale in the zones where it detaches may create deposits, the extent of which disrupts the operation of the furnace and necessitates the shutdown thereof for cleaning. This shutdown time gives rise to losses of production of the plant and is detrimental to its mean profitability over the whole of the year.

The oxide scale that is formed on the surface of the product must be removed before rolling, generally in a descaler that sprays high-pressure water jets on the surface of the product in order to detach the oxide scale by thermal shock and mechanical action of the sprayed water streams.

The oxide scale that is formed on the surface of the steel product may remain adherent, it means that the oxide scale may not be detached from the surface of the steel product, neither in the furnace nor in the descaler, and may follow the product into the various rolling units. This situation may lead to defect on the surface of the finished product or even cause degradations of the rollers of the rolling units or breakages of these rollers.

It is thus understood that the reheating process of a steel product rolling line is greatly influenced by the formation of oxide scale which may have a direct impact on the quality of the finished product and/or a significant influence on the efficiency of the furnace, on its consumption and on the production time between two shutdowns for maintenance.

This situation may be made particularly difficult for flat product furnaces which reheat a large amount of products of different dimensions and different steel grades. The steel products are treated according to heating curves or settings of identical furnaces, which increases the amounts of oxide scale and is detrimental to the heat balance and economic balance of the furnace and also of the whole of the rolling line.

The amount of oxide scale depends on the type of heating carried out in the furnace. FIG. 3 illustrates an example of a heating curve of a product for its total reheating time $t_2$ during its passage through the furnace from charging temperature to the discharge temperature $T_2$. Thus, FIG. 3 presents on the x-axis the heating (useful) length of the furnace, or in an equivalent manner, the residence time of the product in the furnace that it passes through at constant speed. The total residence time equal to $t_2-t_1$, the temperature of the surface of steel product is above a temperature $T_1$, for example of 570° C., starting from which this surface oxidizes under the action of the oxygen present in the corresponding zone of the furnace.

It is understood that the residence time above the oxide scale growth temperature and the content of oxygen present in the combustion gases directly influence the amount of oxide scale and also the its characteristics. These parameters also influence the amount of oxide scale that is detached (or fallen) in the furnace during the reheating of the products, the detachment of the oxide scale in the descaler and the amount of oxide scale remaining on the surface of the products that may give rise to surface defects during the rolling operations.

State Of The Art

The oxide scale growth is considered to be an inevitable component of the steel product reheating process and even if it is recovered this recycling masks costs of forming and treating this oxide scale.

Measuring the oxide scale during the reheating process is carried out by studying samples deposited on the product and reheated with it in the furnace. This method is therefore essentially isolated and does not lend itself to a continuous monitoring of the reheating process for each of the products treated during this process.

Another method for measuring the amount of oxide scale consists in weighing the removed oxide scale in the descaler, in settling tanks of the descaling water or in collection tanks discharged at the overhead crane. This method is not precise since wet oxide scale is weighed and it does not make it possible to measure the oxide scale that is deposited in the furnace but only the oxide scale that is removed from the descaler. Thus, there is an approximation regarding the measurement of the amount of oxide scale. Moreover, the times between weighings of the oxide scale are long, around several hours between two measurements. Lastly, the amounts of oxide scale weighed may correspond to several batches of products reheated in the furnace. Thus, the method is global and therefore approximate.

The methods for measuring the amount of oxide scale according to the state of the art are therefore isolated and approximate. They cannot carry out a continuous monitoring of oxide scale growth in the furnace in order to act in real time on the operating parameters of the furnace.

Oxide scale, when it is taken into account by the operator of the furnace, is managed according to standard settings supposed to provide an average response to this phenomenon irrespective of the dimensions of the products, steel grades and heating cycles carried out.

In particular, furnace setting values are often achieved that increase the amount of oxide scale produced in order to make it possible to be within a comfort zone for operation of the plant for which the oxide scale detaches easily from the product during its passage through the descaler for example, at the expense of the amount of oxide scale produced and of the total cost of formation, collection and treatment of this oxide scale produced.

The furnaces operate with several types of gas, for example natural gas, mixed gas (mixture of several gases) or coke oven gas. These various gases produce different combustion gas compositions, the effects of which on the oxide scale growth are different. These differences are not currently taken into account in the control of the furnaces.

One objective of the invention is to propose a process for controlling a furnace for reheating semi-finished steel products that resolves all or some of the aforementioned drawbacks.

One objective of the invention is to overcome all or some of the drawbacks of the state of the art, and/or to improve the flexibility and simplicity of the control of a reheating furnace while retaining or improving the robustness and the cost of this control, of the maintenance and/or of the operation of the means by which this reheating furnace is controlled.

SUMMARY OF THE INVENTION

At least one of these objectives is achieved with a process for controlling a furnace for reheating semi-finished steel products, comprising:
  a determination, for all or part of a product, of the amount of oxide scale formed by a reheating of the product part, this determination being carried out using data measured relative to the part before and after the reheating,
  a correction of operating parameters of the furnace as a function of the amount of oxide scale thus determined so as to modify the amount of oxide scale formed by the reheating.

Thus, the measurement is carried out using data specific to said product part.

Since the determination is carried out using data measured on said part, the determination of the oxide scale is simplified, the use of sample insertion and removal steps and of physical and human means for carrying out this insertion and removal are avoided.

Of course, the determination of the amount of oxide scale may be carried out for the entire product.

Of course, the data measured after said reheating and relating to said part may be measured after said reheating or after the descaler.

The determination of the amount of oxide scale using data measured on the product before and just after the furnace, that is to say before the descaler, makes it possible to deduce the amount of oxide scale which left in the furnace.

The determination of the amount of oxide scale using data measured on the product before and after the descaler makes it possible to deduce the amount of oxide scale produced during the whole of the process.

It is also possible to optimize the adhesion characteristics of the oxide scale on the product. This optimization makes it possible to reduce the defects on the rolled products.

Advantageously, the determination of the amount of oxide scale in real time is carried out periodically or continuously.

Advantageously, the correction of the operating parameters of the furnace is carried out periodically or continuously.

Unlike the prior art the process according to the invention may be carried out easily, without disturbing the conventional reheating process or rolling process.

Preferably, a determination of the amount of oxide scale and/or a correction of operating parameters of the furnace is carried out for each of the furnace-charged products.

It is thus possible to continuously monitor the oxide scale growth during the heat process in real time.

The determination of the amount of oxide scale may be carried out continuously on all of the products entering and leaving the furnace.

The correction of one or more parameters of the furnace may be carried out continuously according to the information or the data collected by the sensors or devices installed on the furnace.

Thus, the invention provides a solution to the continuous monitoring of oxide scale growth in the furnace so as to optimize the quantity and quality thereof produced. so that it is easily removed the oxide scale from the surface of the products in the descaler and so that this residual amount arriving at the rolling stands is as small as possible.

The control process according to the invention may comprise a determination of the portion of detached oxide scale, for example by the movement of mobile and fixed skids or the supports of the products during the transfer thereof over the entire length of the furnace.

When the portion of detached oxide scale thus determined is greater than a predetermined parameter, for example when this portion is judged to be large, the control process may carry out a modification of the furnace parameters so as to modify the characteristics of the oxide scale at the surface of the product, in particular by increasing the adhesion to the lower skin of the product. This modification may in particular act on a parameter such as the excess air, the residual oxygen in the combustion gases or the injection of steam or by the use of different fuels in various zones of the furnace.

The measurements carried out on a part of the product are performed on this same part of the product before and after the reheating.

According to the invention, the data measured are obtained by measuring the thickness of the product or else its dimensions.

According to a first aspect of the invention, the data measured are obtained by measuring at least one of the dimensions of the product, this measurement being carried out by electromagnetic sensors positioned before and/or after the reheating in order to determine the amount of oxide scale formed at the surface of the product before the descaler.

Preferably, the electromagnetic sensors are oriented so as to observe the lower and/or upper faces of the product.

Preferably, the electromagnetic sensors are positioned so as to observe two parts of one and the same surface of the product, one of the parts of this surface bearing the oxide scale to be measured, the other part of this surface having been cleaned, for example by partial descaling.

Advantageously the electromagnetic sensors are blue laser sensors, i.e. the wavelength of which is between 405 and 473 nm. Blue lasers are specifically well-suited to the temperature level of the products and to the environment in which the sensors are found. Tests carried out with red lasers have shown that these are less accurate when the product is at high temperature levels, for example, around 1250° C. Similarly, tests with white light sensors were less conclusive, the measurements being disturbed by radiations reflected on the product.

The sensors used emit an electromagnetic radiation which scans a sector of the space on a plane P with an angle of view and at a defined frequency. At a time t, they thus see the surface of a transverse edge of the product.

The sensors are advantageously protected by thermal insulation. They are for example placed in heat-insulated and air-conditioned housings, a glass-ceramic window of which allows the passage of the electromagnetic radiation.

According to another aspect of the invention, a step that takes into account the expansion of the product follows a measurement of the thickness of the product.

The determining step of the process according to the invention may use a process for determining the scale loss of at least one part of a steel product, referred to as product, during the passage thereof through a reheating furnace.

According to a second aspect of the invention, a process is proposed for determining the scale loss of at least one part of a steel product, referred to as product, during the passage thereof through a reheating furnace.

The process according to the second aspect of the invention uses a device according to the invention which is described below. The oxide scale fallen from a surface scanned by a sensor is determined by analysis of the relief of the surface obtained by the sensor of the device.

Preferably, the oxide scale present on a surface scanned by a device is determined by analysis of the relief of said surface obtained by said device.

According to a third aspect of the invention, a process is proposed for determining the scale loss of at least one part of a steel product, referred to as product, during the passage thereof through a reheating furnace which can optionally be combined with any other aspect of the invention or one or more of the improvements thereof.

The process according to the third aspect of the invention uses a device according to the invention which is described below. An amount of oxide scale fallen into the descaler is determined by the height difference of the product between upstream and downstream of the descaler determined by the processing of the data provided by the sensors of the device.

Preferably, for each set of two electromagnetic sensors, in order to determine the height of the product, the height between the upper face of the product and the generatrix of the roller determined by the sensor is subtracted from the height of the product determined by the sensor.

According to another aspect of the invention, which can optionally be combined with all or some of the previous aspects, the modification of an operating parameter of the furnace comprises a use of a controlled injection of steam into the furnace. The objective of this modification is to act on oxide scale growth at the surface of the products.

According to another aspect of the invention, which can optionally be combined with all or some of the previous aspects, the modification of an operating parameter of the furnace comprises an increase of the amount of combustion air and/or oxidant injected into the furnace. The objective of this modification is to act on the oxide scale growth at the surface of the products.

According to another aspect of the invention, which can optionally be combined with all or some of the previous aspects, the modification of an operating parameter of the furnace comprises a use of particular atmospheres in various zones of the furnace, in particular of atmospheres having controlled oxygen contents. It is thus possible to obtain residual values of oxygen that correspond to the desired degree of oxidation. The objective of this modification is to modify the quality and quantity of oxide scale.

According to another aspect of the invention, which can optionally be combined with all or some of the previous aspects, the amount of products in the furnace is adjusted as a function of the desired production.

According to another aspect of the invention, which can optionally be combined with all or some of the previous aspects, the modification of an operating parameter of the furnace comprises a use of several types of fuels for supplying the burners of the furnace and producing different atmospheres. The objective of this modification is to reduce the amount of oxide scale.

According to another aspect of the invention, which can optionally be combined with all or some of the previous aspects, an operating parameter of the furnace comprises a use of product heating curves.

According to another aspect of the invention, which can optionally be combined with all or some of the previous aspects, the process according to the invention comprises an optimization of the amount of scale loss in and outside of the furnace during the product reheating process.

According to another aspect of the invention, a device is proposed for determining the scale loss in real time of at least one part of a steel product, referred to as product, during the passage thereof through a reheating furnace located upstream of a descaler, the product preferably moving on roller tables, the device comprising a set of electromagnetic sensors, which set comprises:
 at least one electromagnetic sensor of said set being arranged in order to scan, along a scanning plane, at least in part, the face of the product in the vicinity of the outlet of the furnace, said electromagnetic sensor being oriented so that said scanning plane of the electromagnetic radiation of said sensor is perpendicular to a run direction of the product,
 a set of at least two electromagnetic sensors placed upstream of the descaler and oriented so that the scanning planes of the electromagnetic radiations thereof are substantially on one and the same plane perpendicular to the run direction of said at least one part of the product passing through the generatrix of a roller of a roller table, and a set of at least two electromagnetic sensors placed downstream of the descaler and oriented so that the scanning planes of the electromagnetic radiations thereof are substantially on one and the same plane perpendicular to the run direction of the product passing through the generatrix of a roller of a roller table, said sensors being arranged in order to determine the height of the product upstream and downstream of the descaler.

According to another aspect of the invention, which can optionally be combined with all or some of the previous aspects, the sensors are arranged in order to scan the upper face of the product and the sensors are arranged in order to scan a side face of the product.

According to another aspect of the invention, which can optionally be combined with all or some of the previous aspects, the scanning planes of the electromagnetic radiations of the sensors are inclined at an angle, denoted α, with respect to the longitudinal axis of the rollers of the roller tables.

According to another aspect of the invention, a device is proposed for controlling a furnace for reheating semi-finished steel products, the device being configured in order to implement a control process according to the invention and comprising:

determination means configured in order to determine, for a part of a product, an amount of oxide scale formed by a reheating of said product part, these means being used before and after said reheating, means for correcting an operating parameter of the furnace as a function of the amount of oxide scale formed on the products thus determined, these correction means being configured so as to reduce the amount of oxide scale formed on the products by the reheating.

According to another aspect of the invention, a computer program product is proposed comprising program code instructions for executing the steps of the process according to any one of the claims according to the invention when the program is executed on a computer.

The invention thus makes it possible to optimize, continuously and for each reheated product or periodically on a selection of reheated products, the operation of the furnace by measuring the amount of oxide scale during the passage of the products through the furnace and, from this indication of quality and quantity, to deduce therefrom the optimal settings to be applied to the reheating process in order to reduce the amount of oxide scale and/or to control the oxide scale growth thereof in the furnace to reduce the energy consumption of the plant or reduce the rolling problems of the products after the reheating thereof.

DESCRIPTION OF THE FIGURES

Other distinctive features and advantages of the invention will become apparent on reading the detailed description of uses and embodiments that are in no way limiting, with respect to the appended figures in which.

DESCRIPTION OF THE INVENTION

Since these embodiments are in no way limiting, variants of the invention could in particular be carried out that comprise only a selection of features described subsequently, as described or generalized, isolated from the other features described, if this selection of features is sufficient to confer a technical advantage or to differentiate the invention with respect to the state of the art.

Figure 1:
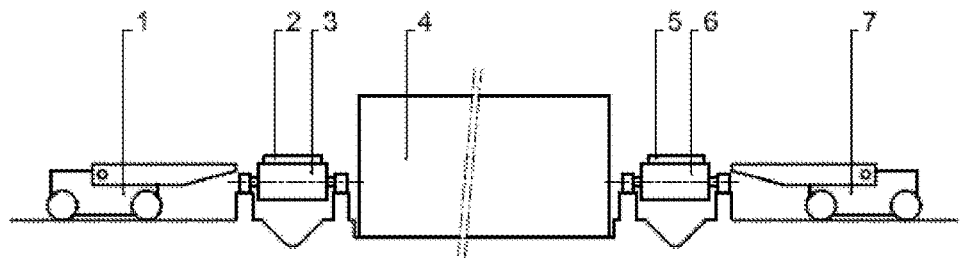
FIG. 1 presents a schematic view of a plant for reheating a steel product.

FIG. 1 presents the principle of a steel product rolling plant. A furnace charging machine 1, for example of finger type, grasps a steel product 2 transported by a roller table 3. The roller table 3 transports the product 2 in front of a furnace 4 for reheating semi-finished steel products. The grasped product 2 is placed by the furnace charging machine 1 in the furnace 4 on transfer frames (not represented).

During its passage through the furnace, the product 2 to be loaded into the furnace is gradually reheated according to a predetermined heating curve, for example in order to be brought from the ambient temperature outside of the furnace 4 typically to a furnace discharge temperature, on leaving the furnace, of between 1100° C. and 1300° C.

A reheated product 5 is removed from the furnace by a finger machine 7 and placed on another roller table 6 which discharges it to a rolling mill (not represented).

Figure 2:
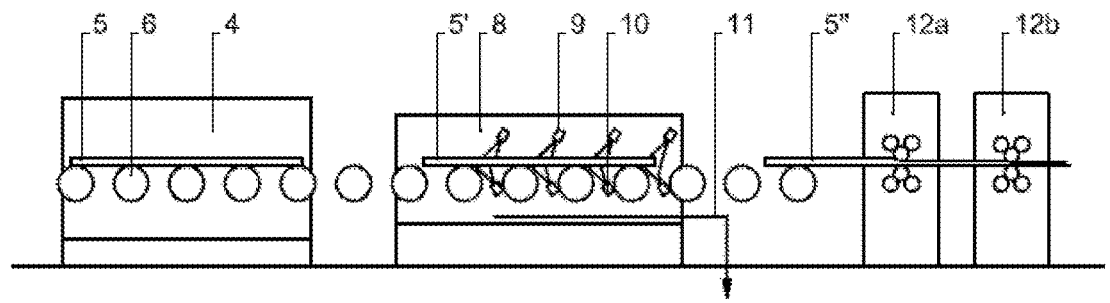
FIG. 2 presents a schematic view of a plant for descaling and rolling the product reheated by the reheating plant.
Figure 3:
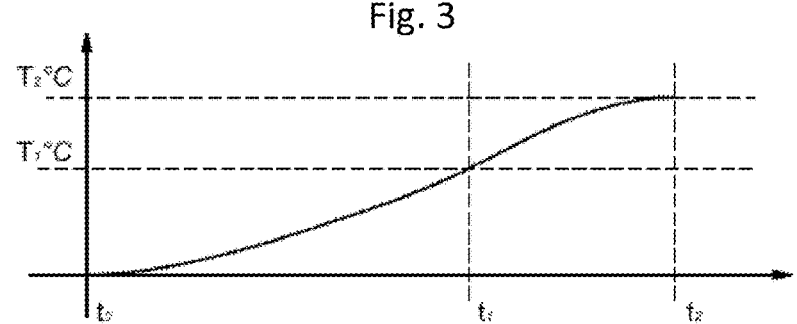
FIG. 3 illustrates an example of a temperature curve of the product during the heating time thereof in the reheating plant.

FIG. 2 shows the roller table 6 for discharging the reheated product 5 after it has left the furnace 4. This product is moved by the roller table 6 to a deoxide scaler 8. In FIG. 2, the product within the deoxide scaler 8 is numbered 5'. The product 5' is exposed, in the deoxide scaler 8, to high-pressure water jets 9, 10. The high-pressure water jets 9, 10 are respectively oriented on an upper and lower part of the product 5'. These water jets 9, 10 are arranged in order to detach the oxide scale formed at the surface of the product 5' and to discharge the detached oxide scale along a circuit 11 to settling tanks (not represented) for the recovery thereof.

After descaling by the deoxide scaler 8, the product is transported to the inlet of a rolling mill. In the rolling mill, the product is referenced 5". The product 5" passes through various rolling sections 12a, 12b. The rolling sections 12a, 12b are arranged in order to obtain a desired wire, section or sheet from the product 5".

In the state-of-the-art plants, the oxide scale recovered in the circuit 11 is weighed in order to define overall the mass recovered and the loss on ignition, that is to say the relative amount of oxide scale produced during the product reheating operation.

According to the invention, a device for continuously measuring the oxide scale produced by the reheating is positioned at the outlet of the furnace 4, optionally after the deoxide scaler. This measurement device is arranged in order to compare the amount of oxide scale to limits set according to the heating method and to the nature of the steel reheated in the furnace.

This comparison makes it possible to deduce a heating efficiency of the furnace and to develop a corrective strategy of the heating suitable for bringing the oxide scale produced back to within the desired quantity and quality limits.

FIGS. 4 to 8 present devices for continuously measuring the oxide scale by measuring its thickness by means of optical distance measurement sensors.

Measurement is carried out by optical analysis on the width of the product and also on the length of the product during the movement thereof in front of the sensor. For each point of the zone scanned by a sensor, that is to say of the surface of the product seen by the sensor, a distance measurement is carried out with an accuracy of the order of a micrometer which enables the measurement of the actual height, that is to say of the thickness of the product.

It is thus easy to calculate the volume of the product, therefore its weight before and after reheating with, by comparison, the amount of oxide scale discharged.

The measurement made also makes it possible to evaluate the thickness of oxide scale formed and, thus, to compensate for the mass of oxide scale that is detached from the product and that has fallen into the furnace and into the deoxide scaler. It is also possible, by calculation, to compensate for the expansion of the products. These calculations may be carried out with simple physical algorithms.

Figure 4:
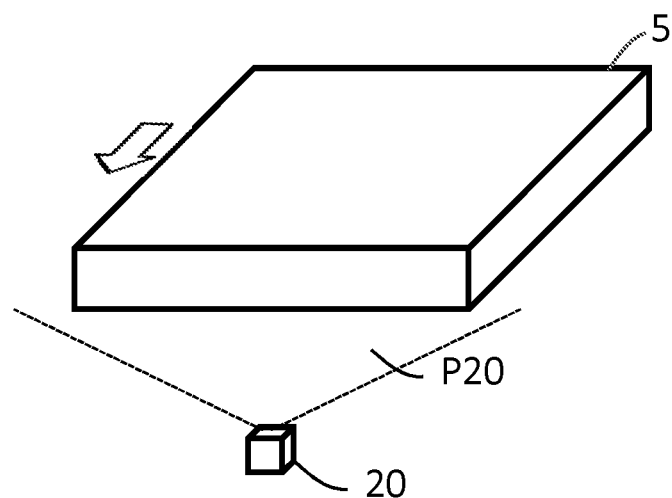
FIG. 4 schematically illustrates the implantation of an electromagnetic sensor that will scan the surface of a product according to the invention.

Seen schematically represented in FIG. 4 is an electromagnetic sensor 20, the electromagnetic radiation of which scans the surface of the lower face of a product 5 while moving over a plane P20 according to an angle of view. In this figure, the product 5 is represented in transverse cross section.

The distance of the sensor with respect to the product and the angle of view of the sensor make it possible to cover the entire width of the product. When the distance of the product and/or the angle of view of the sensor do not make it possible to cover the entire width of the product, several sensors are advantageously used to cover the entire width of the product.

However, in order to limit the cost of the plant, it is possible to only install a single sensor and to use the data collected by this sensor in order to transpose this data onto the surface of the product not covered by the sensor.

It is thus considered, by approximation, that the amount and the features of the oxide scale are the same on the surface covered by the sensor and the surface not covered by the sensor.

A portion of the amount of oxide scale fallen into the furnace 4 is thus determined by at least one sensor 20 placed underneath the product 5, which scans the lower face thereof.

Said sensor is placed at the outlet of the furnace and as close as possible thereto.

The sensor produces a map of the relief of the lower face of the product while this product is running. The analysis of the map of the relief of the surface of the product makes it possible to determine the amount of oxide scale fallen into the furnace. Specifically, the high points at the surface of the product correspond to the locations where the oxide scale is still present on the product. Conversely, the low points correspond to the locations at the surface of the product where the oxide scale has detached and has fallen into the furnace.

The analysis of the data supplied by the sensor makes it possible to determine possible singular points, for example a point substantially higher than the average of the high points. At this point, it is likely that oxide scale has greatly detached from the product but has remained present thereon. The statistical analysis of the data supplied by the sensor makes it possible to take into account these singular points, for example in order to dismiss them during the processing of the data so as not to disturb the determination of the thickness of the oxide scale.

Since the sensor 20 is placed underneath the product, it is necessary to prevent the oxide scale from falling thereon and hampering its operation. For this, a screen 15 that is inclined relative to the ground level is placed between the product 5 and the sensor 20.

This screen must be substantially transparent for the beam so as not to degrade the accuracy of the measurement. It may for example be a glass-ceramic plate.

The inclination of the screen is selected so that the oxide scale that falls onto the screen slides and does not remain thereon.

Since the sensor is placed underneath the screen, it is inclined by the same angle as the screen so as to avoid any optical disturbance of the laser when passing through the screen.

For a finer determination of the loss of oxide scale in the furnace, a sensor is placed on each side of the product leaving the furnace. Just like the sensor placed above the product, these sensors produce a map of the relief of the side faces of the product while this product is running in order to determine the amount of oxide scale formed on said side faces that has fallen into the furnace.

In the case where a single sensor is placed on one of the faces of the product, the total amount of oxide scale lost by the two faces of the product is estimated by doubling that of the instrumented face of the product.

Advantageously according to the invention, a sensor is also placed above the product leaving the furnace so as to produce a map of the upper face of the product. As this oxide scale predominantly remains present on the product leaving the furnace, this map of the upper face is not therefore used to determine the amount of oxide scale fallen into the furnace. This map makes it possible for example to detect a difference in oxidation on the upper face of the products which may be useful for optimizing the operating parameters of the furnace.

Figure 5:
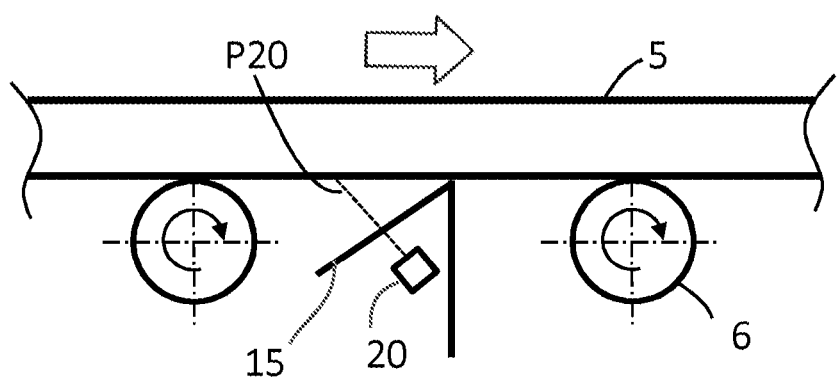
FIG. 5 schematically illustrates the implantation of an electromagnetic sensor that will scan the lower surface of a product according to the invention.

Seen schematically represented in FIG. 5 is a product 5 traveling on a furnace outlet roller table 6 along a longitudinal side view.

An electromagnetic sensor 20 is placed underneath the product. Its electromagnetic radiation scans the surface of the lower face of the product by moving over a plane P20.

An inclined screen 15 is placed between the product and the sensor 20. This screen makes it possible to prevent oxide scale from being deposited on the sensor and hampering its operation.

The sensor 20 is inclined by the same angle as the inclined screen 15 so that the scanning plane P20 of the sensor is perpendicular to the screen 15.

The amount of oxide scale fallen into the deoxide scaler 8 is determined by two sets of sensors, the first set placed upstream of the deoxide scaler, the second set downstream of the deoxide scaler.

Each set of sensors comprises at least a first sensor 30, 40 placed on the upper face of the product and at least a second sensor 31, 41 placed on one of the sides of the product.

The sensors 30 and 31 are placed upstream of the deoxide scaler and the sensors 40 and 41 are placed downstream of the deoxide scaler.

Only the set of sensors 30 and 31 will subsequently be described knowing that the layout of these sensors is identical to that of the sensors 40 and 41.

The sensor 30 placed above the product is positioned in a vertical line with a roller 14 of the roller table on which the products move. It makes it possible to measure the distance between the upper face of the product 5 and the upper generatrix of the roller 14. For a product resting perfectly on the support roller 14, this distance corresponds to the height of the product.

The sensor is placed so that its measuring range covers, at least in part, the upper face of the product and at least one part of the upper generatrix of said roller.

The sensor is advantageously inclined by an angle alpha relative to the longitudinal axis of said roller, for example by an angle of 5°. This inclination makes it possible to guarantee that the beam of the sensor covers, at at least one point 18, the upper generatrix of the roller. Specifically, if the sensor was positioned with its measuring range parallel to the axis of the roller, it would be necessary to have a perfect vertical alignment of the sensor relative to the roller in order for the sensor to see the upper generatrix of the roller and not a generatrix placed on a lower plane. This sensor also makes it possible to measure the relief of the upper face of the product covered by its measuring range.

The sensor placed on the side of the product is positioned on the same vertical plane as the sensor placed above the product, that is to say level with the generatrix of the same support roller. When the sensor placed above the product does not cover the two sides of the support roller located on either side of the product, the sensor placed on the side of the product is located on the side of the roller of which the sensor located on the upper face of the product sees the generatrix.

The sensor placed on the side of the product makes it possible to correct the height of the product measured by the sensor placed on the upper face when the product does not rest exactly on the support roller. Specifically, for a deformed product that would not rest on the generatrix of the roller, the height of the product determined by the upper sensor would correspond to the sum of the actual height of the product to be taken and that of the gap between the lower face of the product and the generatrix of the roller.

The combination of these two sensors enables an accurate measurement of the height of the product. The comparison of the height of the product measured by the first set of sensors positioned upstream of the deoxide scaler and the height measured by the second set of sensors positioned downstream of the deoxide scaler makes it possible to determine the loss of height of the product in the deoxide scaler. This loss of height corresponds to most of the oxide scale fallen into the deoxide scaler.

Sensors placed on the side of the product also make it possible to produce a map of the relief of the face of the product that they scan.

The analysis of the map of the relief of the face of the product makes it possible to determine the amount of oxide scale fallen into the furnace, for the sensor placed upstream of the deoxide scaler, and the amount fallen into the deoxide scaler for the sensor placed downstream of the deoxide scaler. Specifically, the high points at the surface of the product correspond to the locations where the oxide scale is still present on the product. Conversely, the low points correspond to the locations at the surface of the product where the oxide scale has detached and has fallen into the furnace.

When the side sensors are only placed on one of the faces of the product, the total amount of oxide scale lost by the two faces of the product is estimated by doubling that of the instrumented face of the product.

Figure 6:
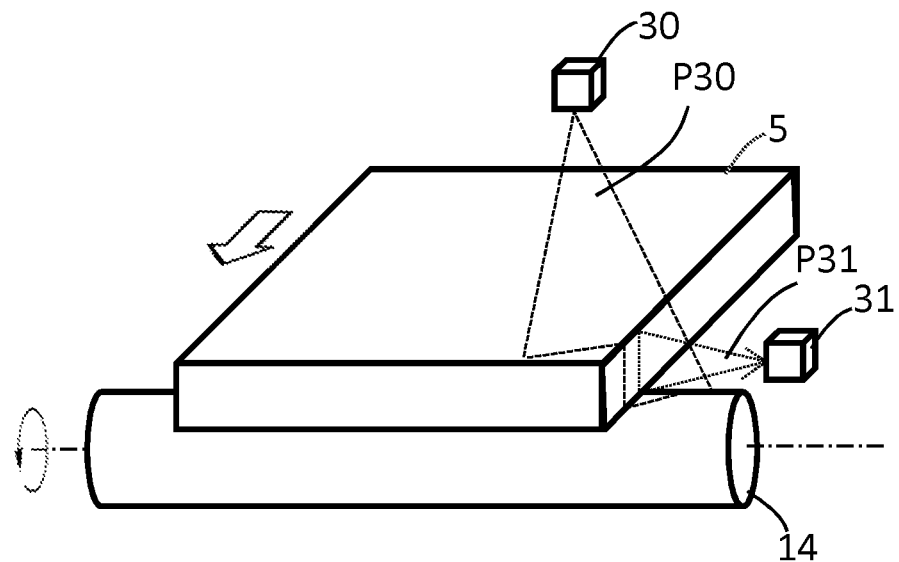
FIG. 6 schematically illustrates the implantation of sensors that will measure the height of a product according to the invention.

Seen represented in transverse view in FIG. 6 is a product 5 traveling on a roller table.

An electromagnetic sensor 30 is placed above the product and scans a portion of the upper face of the product and also a portion of the roller 14 of the roller table located in a vertical line with the sensor.

The plane P30 over which the beam of the sensor moves is perpendicular to the product and substantially parallel to the axis of the roller 14 while being inclined by an angle alpha relative to this axis.

The sensor 30 makes it possible to carry out a first estimation of the height of the product 5 by measuring the distance between the upper face and product and the high point of the generatrix of the roller 14.

An electromagnetic sensor 31 is placed on the side of the product and scans the side face of the product and also a portion of the roller 14.

The plane P31 over which the beam of the sensor 31 moves is perpendicular to the roller and passes through the axis of the roller. The upper generatrix of the roller 14 is thus on the plane P31.

The sensor 31 makes it possible to analyze the relief of the side face of the product and measure a possible space between the edge of the product 5 and the generatrix of the roller 6.

Figure 7:
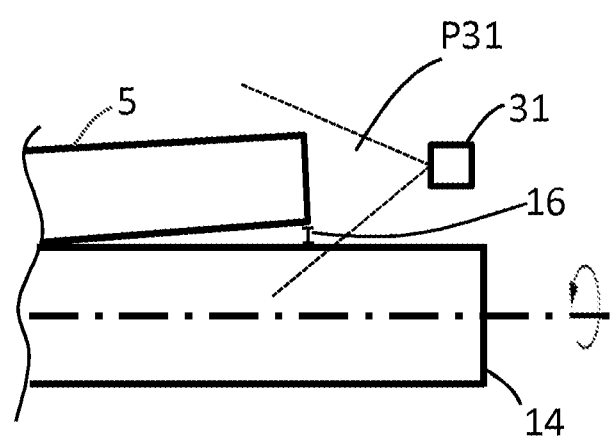
FIG. 7 schematically illustrates the implantation of a sensor according to the invention that will measure the distance between the edge of a product and the roller on which it rests.

Seen represented in transverse view in FIG. 7 is an enlargement of FIG. 6 level with the sensor 31 showing a deformed product 5, the side edge of which does not rest on the roller 14. The sensor 31 thus makes it possible to measure the height 16 of the space between the edge of the product 5 and the generatrix of the roller 14. This height is subtracted from the height of the product determined by the sensor 30 in order to obtain the actual height of the product.

Figure 8:
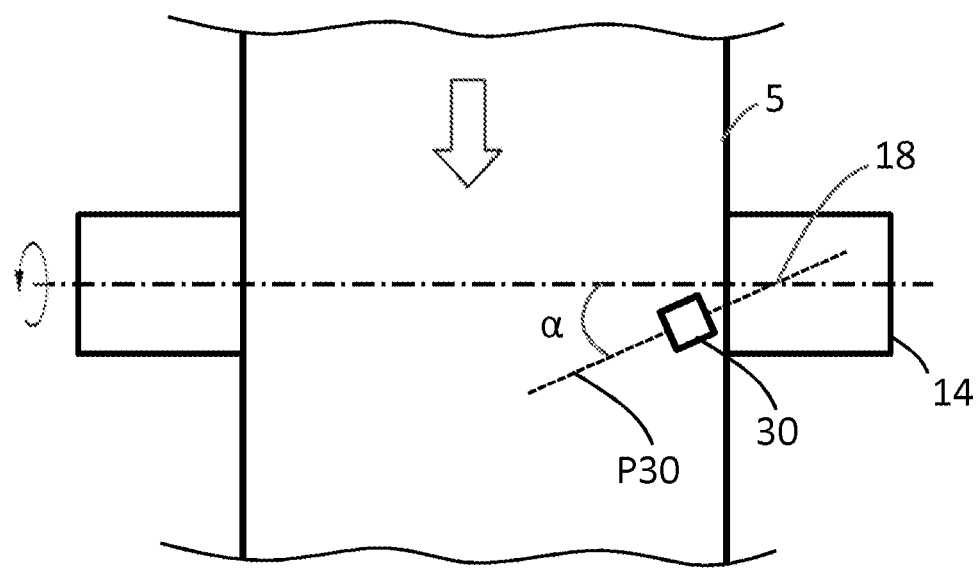
FIG. 8 schematically illustrates the implantation of a sensor according to the invention that will estimate the height of a product.

Seen schematically represented in FIG. 8 in a top view is a product 5 traveling on a roller table, one roller 14 of which is represented.

An electromagnetic sensor 30 is placed above the product and scans a portion of the upper face of the product and also a portion of the roller 14.

The plane P30 over which the beam of the sensor moves is perpendicular to the product and substantially parallel to the axis of the roller 14 while being inclined by an angle alpha relative to this axis. This inclination of the sensor makes it possible to guarantee that the plane P30 passes through the upper generatrix of the roller 14 at a point 18. The sensor 30 thus makes it possible to carry out a first estimation of the height of the product 5 by measuring the distance between the upper face and product and this high point 18 of the generatrix of the roller.

These various devices according to FIGS. 4 to 8 may be used at various steps of the manufacturing process, in particular for demonstrating a difference in the dimensions of the products or in the weight thereof which is representative of the production of oxide scale in terms of amount or behavior thereof.

It is thus possible to demonstrate the amount that may be deposited in the furnace during the reheating or after the furnace during the uptake of the product by the furnace discharging machine or at each step of the process after the furnace, for example during the transfer of the product to the roller tables, in the deoxide scaler or in the various units of the rolling mill.

A person skilled in the art specifically knows how to place such sensors around the furnace. The sensor is protected in a water-cooled housing and aims through a viewing window swept with cold air that maintains it at temperature despite the radiation that it receives from the furnace or from the product.

In particular, the advantage is understood of placing a device for measuring the product before the charging thereof into the furnace and also another after the discharging thereof from the furnace or after the deoxide scaler in order to obtain, from the difference between these measurements, an image of the amount of oxide scale produced and its behavior. It is also possible to carry out several measurements, for example before the furnace, on leaving the furnace and after the deoxide scaler in order to better evaluate the various steps of the life of the oxide scale.

The device described by FIGS. 4 to 8 may be installed at the furnace inlet in order to define a volume model of the product at the furnace charging thereof, it may be installed at the outlet of the furnace or at the outlet of the deoxide scaler in order to produce a volume model of the product after reheating and descaling.

The comparison of the models makes it possible to learn lessons regarding the result of the heating. This teaching may be used in particular to act on the settings of the furnace in order to thereby modify the heating curve and/or the control of the burners and/or the atmosphere in the chamber of the furnace and in particular the excess air and/or a possible injection of steam into certain zones of the furnace and/or to operate the furnace with reducing zones and oxidizing zones and/or to modify the setting parameters of the deoxide scaler such as water pressure, number of descaling ramps used, feed speed of the product.

The capture of this information on the product, before and after reheating, is processed by a computer according to simple or elaborate physical model, for example in order to take into account the behavior of the oxide scale, an evaluation of the portion of the weight of oxide scale that is deposited in the furnace during the reheating, an evaluation of the oxide scale formed at the upper surface of the product and at the lower surface thereof. It is thus possible to take into account the dropping of a portion of the oxide scale formed on the lower face of the product during the transfer thereof on the frames of the furnace or on the discharge roller tables or else an evaluation of the residual portion of oxide scale at the surface of the product after the descaling.

The invention thus proposes a computer program product comprising program code instructions for executing the steps of the process according to any one of the claims according to the invention when the program is executed on a computer.

It is also possible to envisage the use of a computer program product, for example of fuzzy logic or self-adapting type, for continuously analyzing the formation of oxide scale on the product in order to validate the action performed on the operation of the furnace or to evaluate the changes in the oxide scale (in terms of quantity and quality) over time according to the process modifications performed.

It is seen that by means of the continuous measurement of the amount of oxide scale formed at the surface of the product and of the operating system of the furnace by computer, it is possible to continuously adapt the operating parameters of the furnace according to a predefined strategy or predefined objectives, for example to reduce the amount of oxide scale provided, to stabilize the amount of oxide scale produced at a predefined value as a function of the nature of the product to be treated and its treatment process, to modify the amount of oxide scale produced in order to obtain a oxide scale quality suitable for the process, for example for its discharging characteristics in the deoxide scaler.

This process for continuously controlling the furnace according to the measurement of the oxide scale produced makes it possible to optimize the complete rolling process and to optimize the energy consumption by reducing the amount of oxide scale produced.

Of course, the invention is not limited to the examples that have just been described and many adjustments may be made to these examples without departing from the scope of the invention. Furthermore, the various features, forms, variants and embodiments of the invention may be combined with one another in various combinations as long as they are not mutually exclusive or incompatible.

NOMENCLATURE 1 furnace charging machine
2 steel product
3 furnace inlet roller table
4 reheating furnace
5 steel product
5' product in the descaler
5" product in a rolling mill
6 furnace outlet roller table
7 furnace discharging machine
8 descaler
9 upper high-pressure water jet
10 lower high-pressure water jet
11 discharge circuit
12a, 12b rolling sections
14 support roller
15 inclined screen
16 distance between the edge of the product and a support roller
18 intersection between a plane P30 and the upper generatrix of a roller
20 electromagnetic sensor scanning the lower face of a product
30 electromagnetic sensor scanning the upper face of a product upstream of the descaler
31 electromagnetic sensor scanning a side face of a product upstream of the descaler
40 electromagnetic sensor scanning the upper face of a product downstream of the descaler
41 electromagnetic sensor scanning a side face of a product downstream of the descaler
P20 scanning plane of the laser of a sensor 20
P30 scanning plane of the laser of a sensor 30
P40 scanning plane of the laser of a sensor 40
P41 scanning plane of the laser of a sensor 41
P42 scanning plane of the laser of a sensor 42

The invention claimed is:

1. A device for determining the scale loss of at least one part of a steel product (5) during passage of the steel product through a reheating furnace (4) located upstream of a descaler (8), said device comprising:
a set of electromagnetic sensors (20, 30, 31, 40, 41) that includes
a first electromagnetic sensor (20) of said set of electromagnetic sensors arranged to scan, along a first scanning plane, a lower face (50) of the steel product (5) in vicinity of an outlet of the furnace (4), said first electromagnetic sensor oriented so that said first scanning plane (P20) of an electromagnetic radiation of said first electromagnetic sensor is perpendicular to a run direction of the steel product,
second and third electromagnetic sensors (30, 31) of said set of electromagnetic sensors, placed upstream of the descaler (8) and oriented so that scanning planes (P30, P31) of electromagnetic radiation of said second and third electromagnetic sensors are substantially on a same plane (P32) perpendicular to the run direction of the steel product passing through a generatrix of a roller of a first roller table (3), and
fourth and fifth electromagnetic sensors (40, 41) of said set of electromagnetic sensors, placed downstream of the descaler (8) and oriented so that scanning planes (P40, P41) of electromagnetic radiation of said fourth and fifth electromagnetic sensors are substantially on a same plane (P42) perpendicular to the run direction of the steel product passing through a generatrix of a roller of a second roller table (6), each of said second, third, fourth and fifth sensors (30, 31, 40, 41) being arranged so as to determine heights of the steel product upstream and downstream of the descaler.

2. The device as claimed in claim 1, wherein the second and fourth sensors (30, 40) of the set of electromagnetic sensors are arranged to scan an upper face (51) of the steel product (5) and the third and fifth sensors of the set of electromagnetic sensors (31, 41) are arranged to scan a side face (52, 53) of the steel product (5).

3. The device as claimed in claim 1, wherein scanning planes (P30, P40) of the second and fourth sensors (30, 40) are inclined at an angle (α) with respect to a longitudinal axis of the rollers of the first and second roller tables (3, 6).

4. A process for determining scale loss of at least one part of a steel product during passage thereof through a reheating furnace (4), comprising:
using a device comprised of a set of electromagnetic sensors,
the set of electromagnetic sensors including
a first electromagnetic sensor (20) of said set of electromagnetic sensors arranged to scan, along a first scanning plane, a lower face (50) of the steel product (5) in vicinity of an outlet of the furnace (4), said first electromagnetic sensor oriented so that said first scanning plane (P20) of an electromagnetic radiation of said first electromagnetic sensor is perpendicular to a run direction of the steel product,
second and third electromagnetic sensors (30, 31) of said set of electromagnetic sensors, placed upstream of the descaler (8) and oriented so that scanning planes (P30, P31) of electromagnetic radiation of said second and third electromagnetic sensors are substantially on a same plane (P32) perpendicular to the run direction of the steel product passing through a generatrix of a roller of a first roller table (3), and
fourth and fifth electromagnetic sensors (40, 41) of said set of electromagnetic sensors, placed downstream of the descaler (8) and oriented so that scanning planes (P40, P41) of electromagnetic radiation of said fourth and fifth electromagnetic sensors are substantially on a same plane (P42) perpendicular to the run direction of the steel product passing through a generatrix of a roller of a second roller table (6), each of said second, third, fourth and fifth sensors (30, 31, 40, 41) being arranged so as to determine heights of the steel product upstream and downstream of the descaler; and
determining oxide scale fallen from surfaces of the steel product scanned by the first, third, and fifth sensors by analyzing respective reliefs of the surfaces scanned by the first, third, and fifth sensors (20, 31, 41).

5. The process as claimed in claim 4, further comprising:
determining oxide scale present on the surfaces scanned by the first, third, and fifth sensors (20, 31, 41) by analyzing of the respective reliefs of the surfaces obtained by the first, third, and fifth sensors (20, 31, 41).

6. A process for determining scale loss of at least one part of a steel product (5) during passage thereof through a reheating furnace (4), comprising:
using a device comprised of a set of electromagnetic sensors,
the set of electromagnetic sensors including
a first electromagnetic sensor (20) of said set of electromagnetic sensors arranged to scan, along a first scanning plane, a lower face (50) of the steel product (5) in vicinity of an outlet of the furnace (4), said first electromagnetic sensor oriented so that said first scanning plane (P20) of an electromagnetic radiation of said first electromagnetic sensor is perpendicular to a run direction of the steel product,
second and third electromagnetic sensors (30, 31) of said set of electromagnetic sensors, placed upstream of the descaler (8) and oriented so that scanning planes (P30, P31) of electromagnetic radiation of said second and third electromagnetic sensors are substantially on a same plane (P32) perpendicular to the run direction of the steel product passing through a generatrix of a roller of a first roller table (3), and
fourth and fifth electromagnetic sensors (40, 41) of said set of electromagnetic sensors, placed downstream of the descaler (8) and oriented so that scanning planes (P40, P41) of electromagnetic radiation of said fourth and fifth electromagnetic sensors are substantially on a same plane (P42) perpendicular to the run direction of the steel product passing through a generatrix of a roller of a second roller table (6),
each of said second, third, fourth and fifth sensors (30, 31, 40, 41) being arranged so as to determine heights of the steel product upstream and downstream of the descaler; and
determining an amount of oxide scale fallen into the descaler (8) from a height difference of the heights of the steel product (5) upstream and downstream of the descaler as provided by the second, third, fourth, and fifth sensors (30, 31, 40, 41).

7. The process as claimed in claim 6, wherein, heights of the steel product (5) are determined by determining a height between the lower face of the steel product and the generatrix of the roller of the first roller table (3) determined by the third and fifth sensors (31, 41), subtracted from a height of the steel product (5) determined by the second and fourth sensors (30, 40).

8. A process for controlling a furnace (4) for reheating semi-finished steel products (5), comprising:
determining, for at least one part of a steel product (5), an amount of oxide scale formed on the steel products by a reheating of said steel product, said determination comprising the steps of the method recited in claim 4; and
correcting operating parameters of the furnace as a function of the determined amount of oxide scale so as to modify the amount of oxide scale formed by the reheating.

9. The process as claimed in claim 8, wherein the correcting comprises injecting steam into the furnace.

10. The process as claimed in claim 8, wherein the correcting comprises increasing an amount of at least one of combustion air and oxidant injected into the furnace.

11. The process as claimed in claim 8, wherein the correcting comprises using atmospheres having controlled oxygen contents in various zones of the furnace.

12. The process as claimed in claim 8, wherein the correcting comprises using two or more types of fuels for supplying the burners of the furnace and producing different atmospheres.

13. The process as claimed in claim 8, wherein an operating parameter of the furnace comprises a use of product heating curves.

14. The device as claimed in claim 2, wherein scanning planes (P30, P40) of the second and fourth sensors (30, 40) are inclined at an angle (α) with respect to a longitudinal axis of the rollers of the first and second roller tables (3, 6).

* * * * *